United States Patent [19]

Klemarczyk

[11] Patent Number: 5,021,487
[45] Date of Patent: Jun. 4, 1991

[54] THERMALLY STABILIZED ACRYLIC ADHESIVE COMPOSITIONS AND NOVEL METHACRYLATED MALEMIDE COMPOUNDS USEFUL THEREIN

[75] Inventor: Philip Klemarczyk, Collinsville, Conn.

[73] Assignee: Loctite Corporation, Newington, Conn.

[21] Appl. No.: 199,389

[22] Filed: May 27, 1988

[51] Int. Cl.$^5$ .................. C08K 5/3415; C08F 4/32; C08F 22/40; C07D 207/40
[52] U.S. Cl. ..................... 524/104; 526/230; 526/232.5; 526/262; 548/547
[58] Field of Search ............ 524/104; 526/230, 232.5, 526/262; 548/547

[56] References Cited

U.S. PATENT DOCUMENTS

| | | | |
|---|---|---|---|
| 2,895,950 | 7/1959 | Krieble | 260/89.5 |
| 3,043,820 | 7/1962 | Krieble | 260/89.5 |
| 3,218,305 | 11/1965 | Krieble | 260/89.5 |
| 3,988,299 | 10/1976 | Malofsky | 526/262 |
| 4,018,851 | 4/1977 | Baccei | 260/859 |
| 4,089,845 | 5/1978 | Haug et al. | 526/262 |
| 4,107,174 | 8/1978 | Baumann et al. | 260/326 |
| 4,158,730 | 6/1979 | Baumann et al. | 526/262 |
| 4,172,836 | 10/1979 | Baumann et al. | 548/547 |
| 4,247,672 | 1/1981 | Haug et al. | 526/262 |
| 4,284,551 | 8/1981 | Argentar | 260/42.43 |
| 4,287,330 | 9/1981 | Rich | 526/270 |
| 4,295,909 | 10/1981 | Baccei | 156/307 |
| 4,309,526 | 1/1982 | Baccei | 528/75 |
| 4,321,349 | 3/1982 | Rich | 526/260 |
| 4,380,613 | 4/1983 | Nativi | 525/440 |
| 4,439,600 | 3/1984 | Moran, Jr. | 528/392 |
| 4,447,588 | 5/1984 | Rametta | 526/301 |
| 4,661,435 | 4/1987 | Minnema et al. | 430/311 |
| 4,709,050 | 11/1987 | Spivack et al. | 524/104 |

FOREIGN PATENT DOCUMENTS 0208291 7/1986 European Pat. Off. .

OTHER PUBLICATIONS

Gary C. Davis, ACS Symp.-Ser., 242 (Polym. Electron.), 259–269, 1984.

Primary Examiner—Kriellion Morgan
Attorney, Agent, or Firm—Vidas & Arrett

[57] ABSTRACT

The invention comprises a curable acrylic ester formulation which contains a maleimide thermal additive which is essentially miscible in conventional acrylic monomers. The formulation comprises a substantially solvent free adhesive formulation comprising:

a) an acrylic functional maleimide compound of the formula:

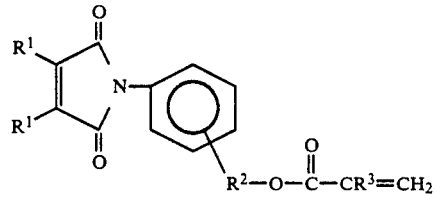

where the $R_1$ groups are independently H or $C_1$-$C_3$ alkyl, $R^2$ is lower alkylene and $R^3$ is defined as for $R^1$;

b) at least one acrylate or methacrylate monomer or prepolymer compound other than a compound as defined in a); and, c) an effective amount of an anaerobic or thermal free radical initiator.

8 Claims, No Drawings

THERMALLY STABILIZED ACRYLIC ADHESIVE COMPOSITIONS AND NOVEL METHACRYLATED MALEMIDE COMPOUNDS USEFUL THEREIN

BACKGROUND OF THE INVENTION

Adhesive and sealant compositions based on acrylate and methacrylate monomers polymerizable by free radical initiation are known in the art. Likewise, anaerobic compositions are known in the art. (See for example U.S. Pat. Nos. 2,895,950, 3,043,820, and 3,218,305). Anaerobic compositions are characterized by their ability to remain liquid in the presence of air but cure to a strong adhesive bond when air is excluded, as by assembling a mated nut and bolt to which the composition has been applied.

While serving many useful purposes, both standard acrylic compositions as well as anaerobic-type acrylic compositions have been limited in applicability due to degradation of adhesive strength at elevated temperatures, e.g., 250° F. or more.

Among the various solutions which have been offered in the art to improve the thermal stability of cured acrylic monomer compositions generally and cured anaerobic compositions in particular, has been the teaching in U.S. Pat. No. 3,988,299 to employ certain maleimide and bismaleimide additive compounds of the formula:

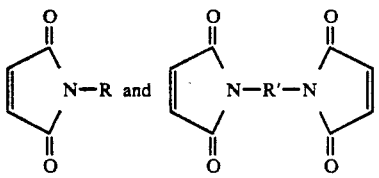

where R and R' are selected from the group consisting of alkyl, cycloalkyl, aralkyl, and alkaryl. The most preferred additive of this type is m-phenylene dimaleimide, sold under the trade name HVA-2.

While the compositions of U.S. Pat. No. 3,988,299 have proved very useful, they do have significant limitations. In particular, the imide additive has a very low solubility in most conventional acrylic monomers. As it is generally desirable to have an imide content higher than the solubility limit in order to see significant improvement in thermal stability properties, it is very difficult to synthesize formulations for commercial use which do not have severe settling problems. Unless thoroughly and uniformly mixed before use such compositions can display erratic and unpredictable cured thermal stability. Moreover, the presence of suspended particulate imide in the formulation may deleteriously effect the strength of ambient temperature cured compositions prior to thermal aging. There is, therefore, a need for an improved thermal additive for curable acrylic compositions which is substantially miscible in conventional acrylic monomers and which has improved thermal aging properties similar to those of the maleimide additives disclosed in U.S. Pat. No. 3,988,299.

SUMMARY OF THE INVENTION

The invention comprises a novel curable acrylic ester formulation which contains a maleimide thermal additive which is essentially miscible in conventional acrylic monomers, including acrylic ester prepolymers conventionally used in anaerobic adhesive formulations. The compositions are substantially solvent-free bulk polymerizable formulations. That is, the cured weights of the formulations of the invention are substantially 100% of the uncured formulation weight. The compositions display substantially improved cured thermal aging properties over compositions not employing the additive, without displaying solubility problems associated with formulations of U.S. Pat. No. 3,988,299.

A further aspect of the invention comprises certain novel maleimide compounds useful as thermal additives in the invention.

DETAILED DESCRIPTION OF THE INVENTION

The thermal additives useful in the compositions of the invention may be represented by the formula:

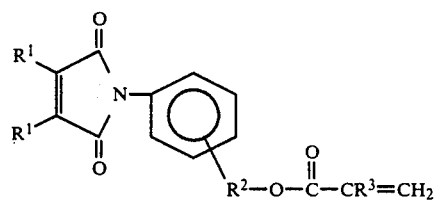

where the $R^1$ groups are independently H or $C_1$–$C_3$ alkyl, $R^2$ is lower alkylene (i.e. $C_1$-about $C_6$) and $R^3$ is defined as for $R^1$. Most preferably the $R^1$ groups are both hydrogen and the $R^2$ group is ethylene.

One class of monomers suited for use in this invention comprises acrylate esters having the following general formula:

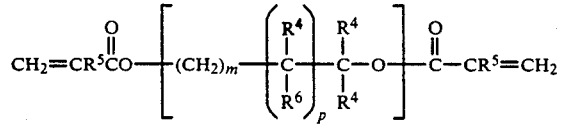

wherein $R^4$ represents a radical selected from the group consisting of hydrogen, halogen, alkyl of 1–4 carbon atoms, inclusive, hydroxy alkyl of 1–4 carbon atoms inclusive, and

$R^5$ is a radical selected from the group consisting of hydrogen, halogen, and lower alkyl of 1–4 carbon atoms; $R^6$ is a radical selected from the group consisting of hydrogen, —OH and

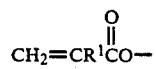

m is an integer equal to at least 1, e.g. from 1 to 8 or higher, for instance, from 1 to 4 inclusive, n is an integer equal to at least 1, for example, 1 to 20 or more; and p is 0 or 1.

The polymerizable polyacrylate esters utilized in accordance with the invention and corresponding to the above general formula are exemplified by, but not restricted to, the following materials: diethylene glycol dimethacrylate. triethylene glycol dimethacrylate, tetraethylene glycol dimethacrylate, dipropylene glycol dimethacrylate, di(pentamethylene glycol) dimethacrylate, tetraethylene diglycerol diacrylate, diglycerol tetramethacrylate, tetramethylene dimethacrylate, ethylene dimethacrylate, neopentyl glycol diacrylate and trimethylol propane triacrylate. Of these, the preferred monomers are triethylene glycol dimethacrylate and polyethylene glycol dimethacrylate.

In addition to the monomers described above, epoxy acrylate monomers (i.e. the reaction products of epoxy compounds or prepolymers with acrylic or methacrylic acids) and urethane acrylate capped prepolymers such as those described in U.S. Pat. Nos. 4,309,526, 4,295,909, 4,018,851, 4,380,613, and 4,439,600 may be employed.

Although di-and and other polyacrylate esters are preferred, monoacrylate esters can be used, particularly if the non-acrylate portion of the ester contains a hydroxyl or amino group, or other reactive substituent which serves as a site for potential crosslinking. Examples of monomers of this type are hydroxyethyl methacrylate, cyanoethyl acrylate, t-butylaminoethyl methacrylate and glycidyl methacrylate Further details on useful monomers may be found in U.S. Pat. No. 4,287,330 at Col. 3, line 51—Col. 6, line 44.

The preferred compositions include at least one monomer or prepolymer which is characterized by at least two acrylate or methacrylate groups per molecule. Such compounds are suitably used at levels of 30% or more by weight of the composition. The improved thermal properties of the inventive compositions are usually most striking when the formulation contains a urethane acrylate or urethane methacrylate capped prepolymer.

The compositions of the inventions cure via a free radical mechanism. Typical of the useful initiators are any of a wide variety of known peroxy initiators. Illustrative of such initiators are the diacyl peroxides such as benzoyl peroxide; dialkyl peroxides such as di-t-butyl peroxide; ketone peroxides such as methylethyl ketone peroxides; and peresters which readily hydrolyze, e.g., t-butyl peracetate, t-butyl perbenzoate, di-t-butyl diperphthalate, etc. A particularly useful class of peroxy initiators are the organic hydroperoxides such as cumene hydroperoxide, methyl ethyl ketone hydroperoxide, t-butyl hydroperoxide, etc. Of these, cumene hydroperoxide is especially preferred. The initiators should be used at a concentration of about 0.01% to about 10% by weight of the total formulation, preferably 0.1% to about 5% by weight, most preferably about 1%–3% by weight.

In place of peroxide compounds, effective amounts of other free radical initiator compounds which are activated thermally or by anaerobic conditions may be employed. Examples of such compounds are azonitrile initiators, benzopinacol and substituted benzopinacol, and certain halogen containing compounds having electronic structures which facilitate free radical formation as described in detail in U.S. Pat. No. 4,447,588, incorporated herein by reference.

Accelerators of anaerobic polymerization may also be advantageously included. Such accelerators include a variety of secondary and tertiary organic amines as well as sulfimides (e.g. benzoic sulfimide) which are also known in the art. These may be used at a concentration range of about 0.1 to about 5, preferably about 1 to about 2% by weight of the total composition. Preferred accelerators are the hydrazine derivatives described in U.S. Pat. No. 4,321,349, incorporated herein by reference, especially 1-acetyl 2-phenyl hydrazine.

Other agents such as thickeners, plasticizers, etc., are also known in the art and may advantageously be incorporated where functionally desirable, provided only that they do not interfere with the functioning of the additive for its intended purpose. This, of course, can be determined by simple experimentation.

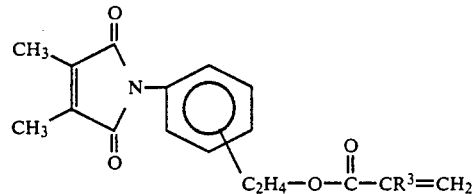

appear to be within the scope of the general formulas for monomers used to prepare polymers useful as photoresist materials which are given in U.S. Pat. No. 4,107,174. Preparation of such polymers necessitates a selective reaction of the methacrylate group to prepare a polymer which retains the more sterically hindered maleimide double bond as a site for photocrosslinking.

An aspect of the invention pertains to the novel maleimides which are the preferred additive compounds of the invention. The preferred compounds of this invention differ from those of the formula above in that there is no steric hindrance of the maleimide double bond. These preferred compounds may be represented by the formula:

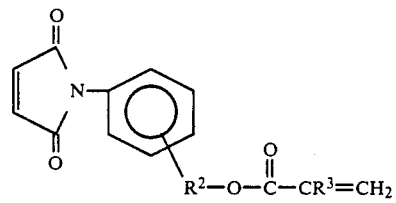

Because of the absence of steric hinderance at the maleimide double bond it is not possible to selectively polymerize the methacrylate groups as required for the utility disclosed in U.S. Pat. No. 4,107,174. This difference in reactivity is demonstrated in Examples 5 and 6 below. Thermal additive compounds where the $R^1$ groups are both methyl provide comparable thermal stability enhancement in the inventive formulations to the preferred compounds where the $R^1$ groups are both H. However, the preferred compounds are believed to be more advantageous in the adhesive compositions of the invention because their greater reactivity will permit the maleimide structure to crosslink into the cured polymer at lower initial temperatures. Such a property is important if the adhesive is required to cure and display structural bonding characteristics before being subjected to elevated temperatures.

The invention is illustrated by the following non-limiting examples.

EXAMPLE 1

(Preparative Example)

A 2000 ml flask, equipped with a mechanical stirrer, condenser, thermometer heating mantle, nitrogen inlet, and an addition funnel, was charged with hydroxyethylaniline (100 g, 0.73 mole) and 750 ml of acetone. Maleic anhydride (71.5 g, 0.73 mole) was dissolved in 250 ml of acetone and this solution was added dropwise to the reaction mass over a 15 minute period. A yellow precipitate formed and an exotherm to 32° C. was noted. After stirring this mixture for 30 minutes at room temperature, triethylamine (20 ml) and nickel(II)acetate (1.2 g, 6.7 mmol) were added and the reaction mixture was heated to reflux. Acetic anhydride (78.1 g, 0.77 mole) was added dropwise over a 15 minute period. After the addition was complete all solids dissolved, and the reflux was continued for three hours. Water (5 ml) was added to quench excess acetic anhydride, and the solution was cooled and filtered to remove a fine precipitate. Solvent was removed under reduced pressure and the residue was added to 2000 ml of 5% aq. $Na_2CO_3$ which was cooled in an ice bath. The product precipitated and was collected by filtration. The crude product was dissolved in 1000 ml of methylene chloride and washed twice with 500 ml of water. The organic layer was separated, dried ($MgSO_4$) and filtered. Solvent was removed under reduced pressure, and the product was used in the next step without further purification. Spectral data (NMR and IR) were consistent with the desire product, 4-(2-hydroxyethyl)phenyl maleimide.

EXAMPLE 2

(Preparative Example)

A 2000 ml flask, equipped with a mechanical stirrer, condenser, thermometer, nitrogen inlet and a Dean-Stark trap, was charged with 4-hydroxyethylphenyl maleimide (107.4 g, 495 mmol), toluene (750 ml), methacrylic acid (85.1 g, 0.99 mole), methanesulfonic acid (5.0 g, 52 mmol) and BHT (1.5 g). This solution was heated to reflux, and after 4 hours, evolution of water ceased. The reaction was cooled and washed consecutively with 1000 ml each of 5% aq. $Na_2CO_3$, 2% aq. $Na_2CO_3$ and twice with water. The organic layer was separated, dried ($MgSO_4$) and filtered. To this solution was added 50 g of acidic alumina and 10 g of activated carbon to remove trace amines. The mixture was stirred for 3 hours, and filtered through a pad of acidic alumina. Solvent was removed under reduced pressure, and the produce was dried for 3 hours at 75° C. and 0.5 mm/Hg. Spectral data (NMR & IR) were consistent with the desired product, 4-(methacryloxyethyl)phenyl maleimide.

EXAMPLE 3

A base resin formulation was prepared as follows:

| Ingredient | Parts by Weight |
|---|---|
| Urethane acrylate capped polyethyleneoxide-2000 | 69.8 |
| isobornyl methacrylate | 7.4 |
| lauryl methacrylate | 12.3 |
| acrylic acid | 5.0 |
| acetyl phenyl hydrazine | 1.0 |
| Saccharin | 1.0 |
| Cumene hydroperoxide | 2.0 |
| 5% napthoquinone in polyethyleneglycol dimethacrylate | 0.2 |
| 3% $Na_4$ EDTA in 80:20 methanol/$H_2O$ | 1.0 |

To 10.0 parts of the base resin formulation was added 3.0 parts hydroxypropyl methacrylate to form a control adhesive composition. A composition utilizing the prior art maleimide, HVA-2, was prepared by adding 3.0 parts hydroxypropyl methacrylate and 1.0 part HVA-2 to 10.0 parts of the base resin. The HVA-2 did not dissolve in the formulation. A composition of the invention was prepared by adding 4.0 parts of a 25% soln of the product of Example 2 in hydroxypropyl methacrylate to 10.0 parts of the base resin.

Test specimens were prepared by bonding steel lap shear coupons in accordance with ASTM D2002, curing the adhesive for 18 hours at 93.3° C. Heat age studies were performed by determining tensile shear strengthens after the 18 hour cure period and after aging the bonded assemblies for 1, 2, 3, and 4 week intervals of 204° C.

The results, shown in Table I, demonstrate that the formulation employing the methacrylate maleimide substantially improved heat aging performance over the control and even out performed the HVA-2 formulation until the third week.

TABLE I

| Heat Age Studies Urethane Acrylate System Tensile Shear Strengths (PSI) | | | |
|---|---|---|---|
| Week | No Maleimide | HVA-2 | Example 2 Maleimide |
| 18 hrs | 3277 | 3387 | 3668 |
| 1 | 745 | 1240 | 1550 |
| 2 | 0 | 856 | 1284 |
| 3 | — | 488 | 3 |
| 4 | — | 0 | 0 |

EXAMPLE 4

Heat age studies were conducted as in Example 3 using an ethoxylated bisphenol A methacrylate system in place of the urethane acrylate system of Example 3. The results, shown in Table II, again demonstrate the effectiveness of the soluble methacrylated maleimides of the invention in improving heat age performance of the base adhesive.

TABLE II

| Heat Age Studies Ethoxylated Bisphenol A Methacrylate System Tensile Shear Strengths | | | |
|---|---|---|---|
| Week | No Maleimide | HVA-2 | Example 2 Maleimide |
| 18 hrs | 1879 | 2002 | 1711 |
| 1 | 2421 | 2480 | 2297 |
| 2 | 1863 | 2047 | 2393 |
| 3 | 1757 | 2200 | 2009 |
| 4 | 1026 | 2380 | 2469 |

EXAMPLE 5

(Comparative Example) A 100 ml round bottom flask equipped with a stirrer, condenser, thermometer and heating mantle was charged with the maleimide of the formula:

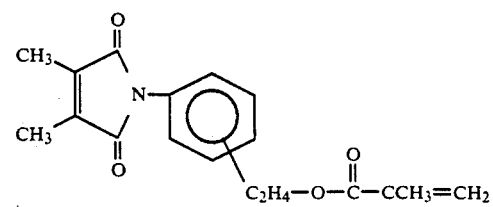

(5.5 g, 17.5 mmol), AIBN (0.04 g, 0.25 mmol) and 50 ml of THF under nitrogen. The solution was heated to reflux (ca. 67° C.) After refluxing with stirring for five hours, the solution was cooled and added to 5000 ml of hexane. The polymer precipitated, was filtered, and washed with hexane. The product was soluble in common organic solvents demonstrating that a linear uncrosslinked polymer had been produced.

EXAMPLE 6

(Comparative Example)

A 100 ml round bottom flask, equipped in the same way as above, was charged with the maleimide:

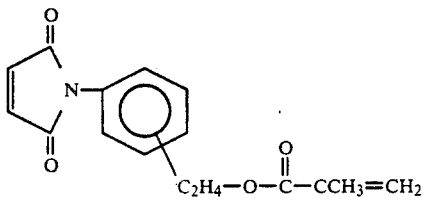

(5.0 g, 17.5 mmol), AIBN (0.04 g, 0.25 mmol), and 50 ml of THF under nitrogen. The solution was heated to reflux (ca. 67° C.). After 30 minutes of reaction, a sudden crosslinking occurred with a strong exotherm. Some of the reactants were expelled from the reaction flask. The reaction was immediately cooled and added to 500 ml of hexane. The remaining polymer was filtered, washed with hexane, and vacuum dried for two hours at 5.0 mm/Hg and 50° C. The recovered polymer was insoluble in common organic solvents, but did swell on addition of solvent, indicating that the polymer was crosslinked.

I claim:

1. A substantially solvent free adhesive formulation comprising:
   a) an acrylic functional maleimide compound of the formula:

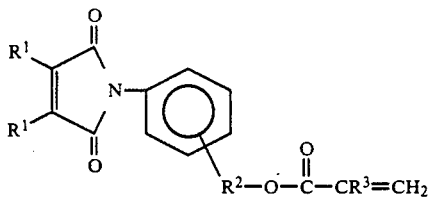

where the $R^1$ groups are independently H or $C_1$-$C_3$ alkyl, $R^2$ is $C_1$-$C_6$ alkylene, and $R^3$ is defined as for $R^1$.
   b) at least one other acrylate or methacrylate compound or prepolymer compound other than that defined in a) provided that when $R^1$ is $C_1$-$C_3$ alkyl, said other acrylate or methacrylate compound is a di- or poly-acrylate or methacrylate; and,
   c) an effective amount for initiating polymerization of an anaerobic or thermal free radical initiator.

2. A composition as in claim 1 wherein the free radical initiator is a peroxide compound.

3. A composition as in claim 1 wherein the maleimide compound has the formula:

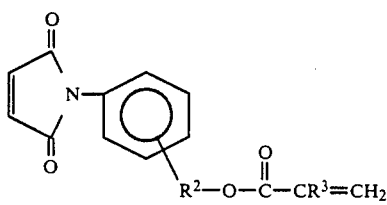

4. A composition as in claim 3 wherein $R^3$ is ethylene.

5. A compound of the formula:

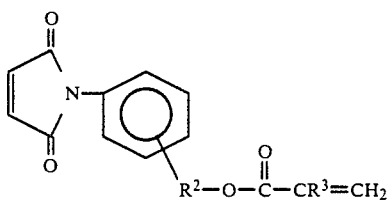

wherein $R^2$ is $C_1$-$C_6$ alkylene and $R^3$ is H or $C_{1-3}$ alkyl.

6. A compound as in claim 5 wherein $R^2$ is ethylene and $R^3$ is H or methyl.

7. A method of improving the cured heat aging properties of an anaerobic or heat cureable acrylic adhesive, the method comprising adding an amount effective for enhancing the cured heat aging properties of the adhesive of a compound of the formula:

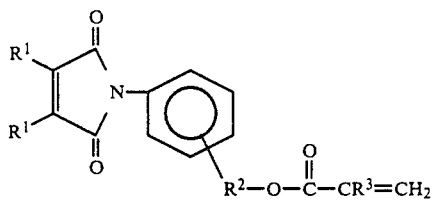

where the $R^1$ groups are independently H or $C_1$-$C_3$ alkyl, $R^2$ is $C_1$-$C_6$ alkylene, and $R^3$ is defined as for $R^1$ to said adhesive prior to curing.

8. A method as in claim 7 wherein the $R^1$ groups are H and $R^3$ is H or methyl.

* * * * *